United States Patent
Berzosa Rodríguez et al.

US008829023B2

(10) Patent No.: US 8,829,023 B2
(45) Date of Patent: Sep. 9, 2014

(54) PROCESS FOR OBTAINING COMPOUNDS DERIVED FROM TETRAHYDRO-β-CARBOLINE

(75) Inventors: Xavier Berzosa Rodríguez, L'Hospitalet del Llobregat (ES); Francisco Marquillas Olondriz, Barcelona (ES)

(73) Assignee: Interquim, S.A., Sant Cugat del Vallès (ES)

( * ) Notice: Subject to any disclaimer, the term of this patent is extended or adjusted under 35 U.S.C. 154(b) by 0 days.

(21) Appl. No.: 13/984,458

(22) PCT Filed: Feb. 10, 2012

(86) PCT No.: PCT/EP2012/052281
§ 371 (c)(1),
(2), (4) Date: Aug. 8, 2013

(87) PCT Pub. No.: WO2012/107549
PCT Pub. Date: Aug. 16, 2012

(65) Prior Publication Data
US 2013/0324730 A1    Dec. 5, 2013

(30) Foreign Application Priority Data
Feb. 10, 2011   (ES) .................................. 201130177

(51) Int. Cl.
A01N 43/42   (2006.01)
A61K 31/44   (2006.01)
C07D 221/18   (2006.01)
C07D 471/00   (2006.01)
C07D 498/00   (2006.01)
C07D 515/00   (2006.01)
C07D 221/22   (2006.01)
C07D 221/06   (2006.01)
C07D 491/00   (2006.01)
C07D 471/14   (2006.01)
C07D 471/04   (2006.01)
(52) U.S. Cl.
CPC .................................. C07D 471/14 (2013.01);
C07D 471/04 (2013.01)

USPC ........... 514/287; 514/292; 514/284; 514/290; 546/64; 546/84; 546/79; 546/61

(58) Field of Classification Search
USPC ............................................ 546/64; 514/287
See application file for complete search history.

(56) References Cited

U.S. PATENT DOCUMENTS 7,223,863 B2    5/2007   Deshpande et al.

FOREIGN PATENT DOCUMENTS

| EP | 070668 B1 | 7/1998 |
| EP | 1546149 B1 | 11/2008 |
| EP | 2 107 059 A1 | 10/2009 |
| EP | 2107059 A1 | 10/2009 |
| EP | 2170880 B1 | 8/2012 |
| WO | WO 2004/011463 A1 | 2/2004 |
| WO | WO 2005/068464 A2 | 7/2005 |
| WO | WO 2006/110893 A2 | 10/2006 |
| WO | WO 2007/052283 A1 | 5/2007 |
| WO | WO 2009/004557 A2 | 1/2009 |
| WO | WO 2009/047613 A2 | 4/2009 |
| WO | WO 2009/144734 A1 | 12/2009 |
| WO | WO 2009/148341 A1 | 12/2009 |

OTHER PUBLICATIONS

Liu; Synthetic Communications, 2007, 37, 3933-3938.*
International Search Report mailed on May 25, 2012, issued in PCT/EP2012/052281.
Written Opinion of the International Searching Authority mailed on May 25, 2012, issued in PCT/EP2012/052281.
English translation of the Specification of IN-00307CH2003-A published on Jul. 27, 2007.

* cited by examiner

Primary Examiner — John Mabry
Assistant Examiner — Daniel Carcanague
(74) Attorney, Agent, or Firm — Birch, Stewart, Kolasch & Birch, LLP

(57) ABSTRACT

The invention relates to a process for obtaining compounds derived from tetrahydro-β-carboline, specifically tadalafil and intermediate products from the synthesis, comprising the reaction between piperonal and an alkyl ester of D-tryptophan as a salt, and in the absence of any other component, followed by haloacetylation and a final cyclization with methylamine.

16 Claims, No Drawings

PROCESS FOR OBTAINING COMPOUNDS DERIVED FROM TETRAHYDRO-β-CARBOLINE

This invention relates to a process for compounds derived from tetrahydro-β-carboline, specifically tadalafil (7) and intermediate products from the synthesis. Tadalafil (7) corresponds chemically to (6R,12aR)-2,3,6,7,12,12a-hexahydro-2-methyl-6-(3,4-methylendioxiphenyl)-pyrazino-[2',1':6,1]pyrido[3,4-b]indol-1,4-dione and is a selective inhibitor of the phosphodiesterase-5 of the cyclic guanosine monophosphate, used for treatment of erectile dysfunction. Its structural formula is:

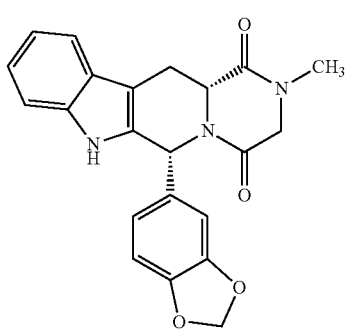

7

STATE OF THE ART

There are numerous patents that describe how to obtain 7 from the methyl ester of D-tryptophan (1) (or its hydrogen chloride, 1HCl) and piperonal (2), the reaction between the two being the key step in the process for obtaining 7.

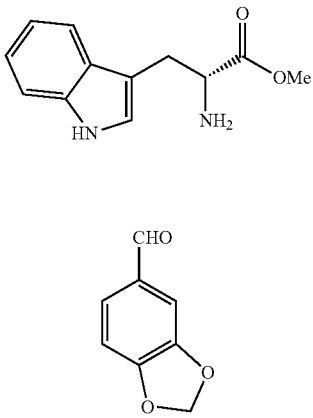

1

2

The product patent EP0740668B1 describes as a first step the reaction between 1 and 2 in dichloromethane (DCM) in the presence of trifluoroacetic acid (TFA). The best results are obtained by reaction for 5 days at 4° C., producing 3 with a yield of 69.8%. The desired isomer (3cis) is then isolated by crystallisation, with a yield of 42.2%. It also describes epimerisation processes for transforming 3trans into 3cis by heating in aqueous or methanolic HCl. The yield obtained in the best of cases is of 72% by heating in aqueous HCl at 60° C. for 36 h. The process for obtaining tadalafil is shown in FIG. 1.

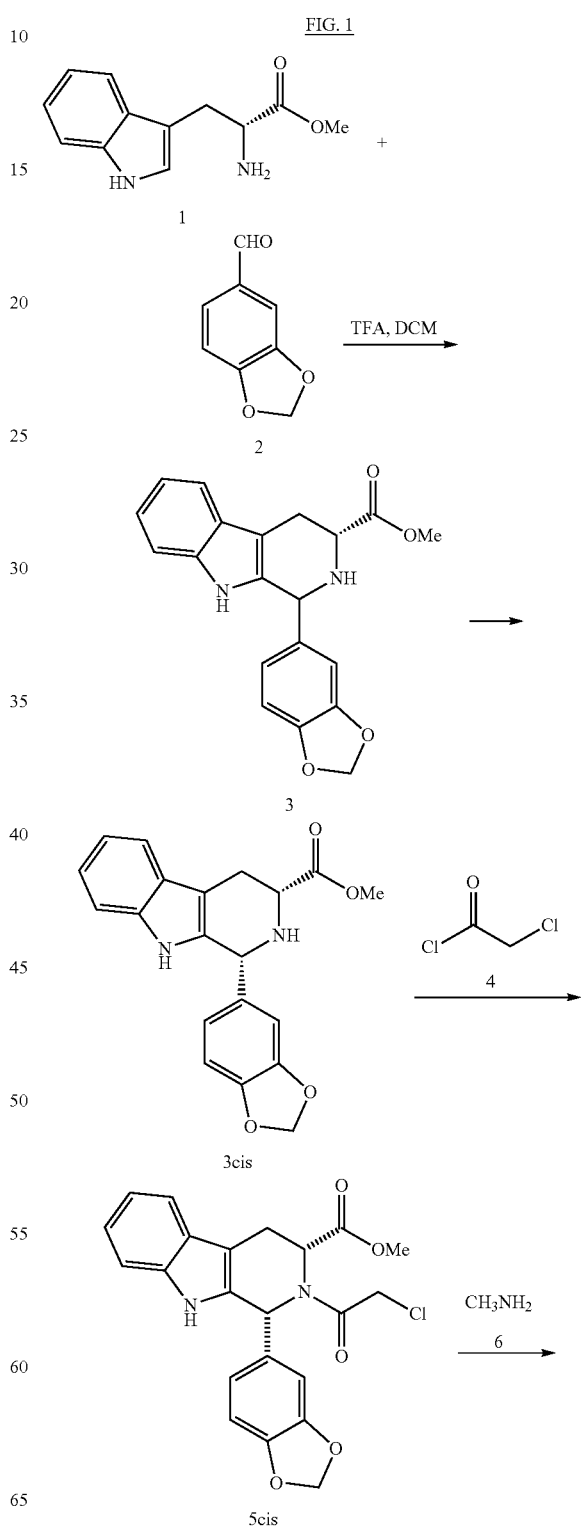

FIG. 1

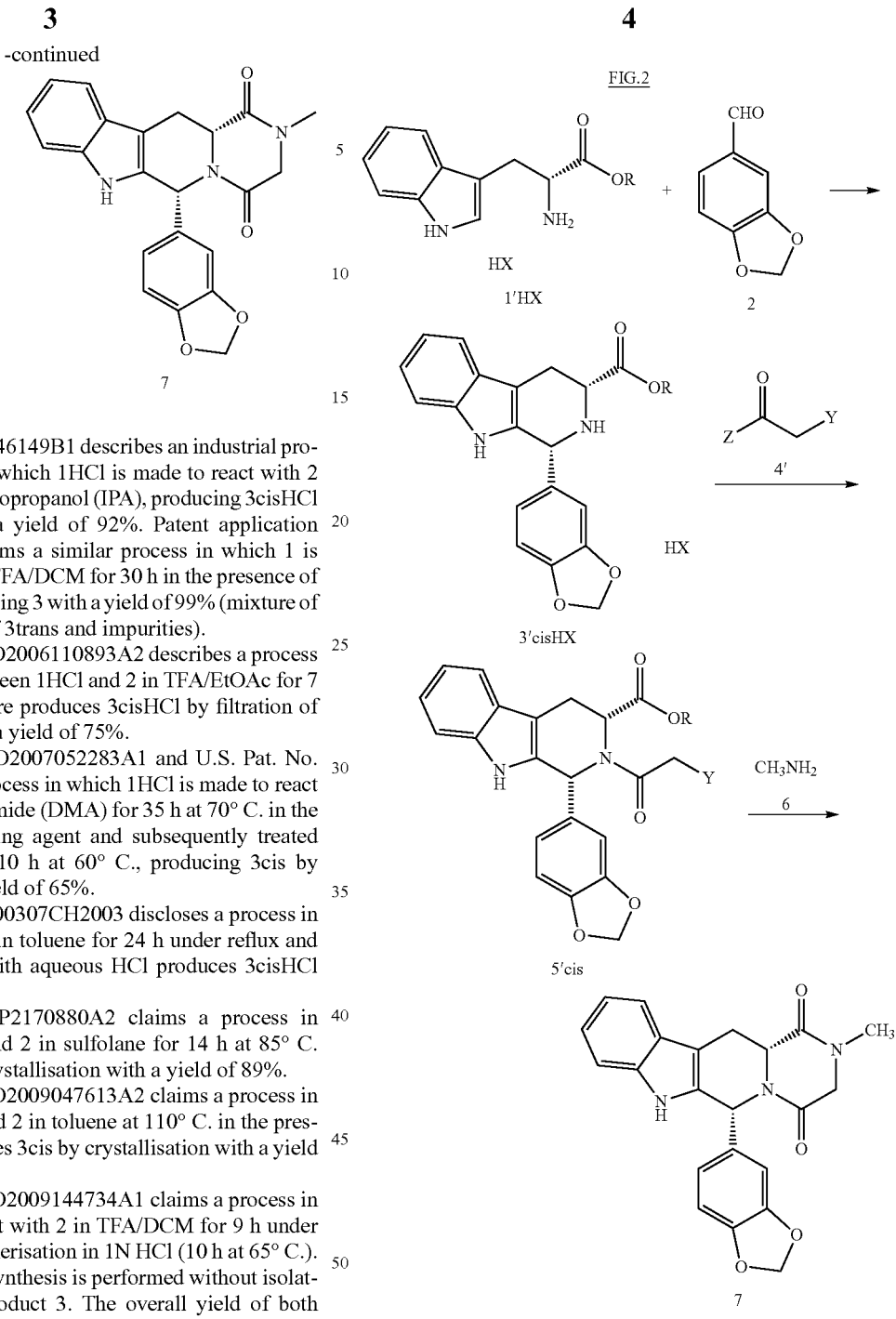

FIG.2

The later patent EP1546149B1 describes an industrial process for obtaining 7, in which 1HCl is made to react with 2 under reflux for 18 h in isopropanol (IPA), producing 3cisHCl by precipitation, with a yield of 92%. Patent application WO2005068464A2 claims a similar process in which 1 is made to react with 2 in TFA/DCM for 30 h in the presence of molecular sieves, producing 3 with a yield of 99% (mixture of 60.4% of 3cis, 26.9% of 3trans and impurities).

Patent application WO2006110893A2 describes a process in which a reaction between 1HCl and 2 in TFA/EtOAc for 7 days at room temperature produces 3cisHCl by filtration of the reaction crude with a yield of 75%.

Patent documents WO2007052283A1 and U.S. Pat. No. 7,223,863B2 claim a process in which 1HCl is made to react with 2 in dimethylacetamide (DMA) for 35 h at 70° C. in the presence of a dehydrating agent and subsequently treated with aqueous HCl for 10 h at 60° C., producing 3cis by crystallisation with a yield of 65%.

Patent application IN00307CH2003 discloses a process in which reacting 1 and 2 in toluene for 24 h under reflux and subsequent treatment with aqueous HCl produces 3cisHCl with a yield of 80%.

Patent application EP2170880A2 claims a process in which reacting 1HCl and 2 in sulfolane for 14 h at 85° C. produces 3cisHCl by crystallisation with a yield of 89%.

Patent application WO2009047613A2 claims a process in which reacting 1HCl and 2 in toluene at 110° C. in the presence of PEG400 produces 3cis by crystallisation with a yield of 65%.

Patent application WO2009144734A1 claims a process in which 1 is made to react with 2 in TFA/DCM for 9 h under reflux, followed by epimerisation in 1N HCl (10 h at 65° C.). The second step of the synthesis is performed without isolating the intermediate product 3. The overall yield of both stages is 53%.

According to the processes described above, the production of tadalafil (7) presents an important problem, which is the considerable period of time required for the reaction between the D-tryptophan ester (1) (or its hydrogen chloride, 1HCl) and piperonal (2). This reaction is the key of the entire process and requires improvement in order to achieve a cheaper and more effective industrial process.

SUMMARY OF THE INVENTION

The invention provides a new and advantageous industrial process for producing compounds derived from tetrahydro-β-carboline, specifically tadalafil (7) and its intermediate synthesis products, according to the diagram in FIG. 2.

The main characteristic of this invention consists in that the reaction between piperonal (2) and D-tryptophan alkyl esters as salts with HX hydracids (1'HX), can be performed without requiring the addition of any other component (solvent, acid, catalyst, desiccant . . . ) to produce compounds of formula 3'cisHX. Said compounds are produced with good yields simply from piperonal and 1'HX, carrying out the reaction at a temperature above the melting point of piperonal (35° C.). The reaction temperature can be adjusted between 75 and 150° C. and preferably between 110 and 130° C. The reaction can be performed with any ratio between the reagents, but the applicants have discovered that the operation is conveniently performed at a molar ratio 1'HX:2 of 1:1 to 1:6 and more preferably between 1:2 to 1:5, a fact that improves the flowability of the system, without prejudice to the use of greater proportions. It is remarkably observed that the reaction time is drastically reduced with respect to that described in the state of the art.

The reaction can also be performed at low temperatures (40-75° C.) then producing a reaction crude formed by a mixture of the 3'cisHX and 3'transHX diastereoisomers of the 3'HX compound (FIG. 3).

(FIG. 3)

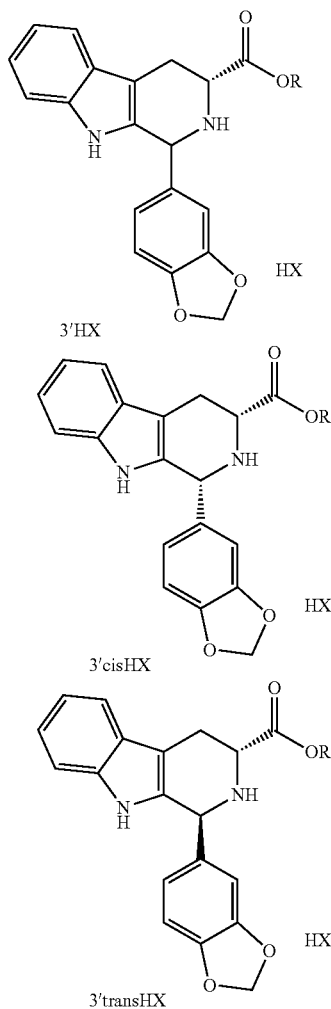

When this reaction crude is heated to 110-130° C. for a brief period of time (15-30 minutes), it produces only the intended isomer (3'cisHX). We would like to highlight that the epimerisation processes described above involve a minimum reaction time of 8 h. Therefore, if the reaction is performed directly at 110-130° C., it essentially produces 3'cisHX.

The fact of not adding any other components to the reaction in the step of producing the 3'cisHX compounds and the non-interference of the presence of piperonal (2) in the following step of the synthesis to produce the 5'cisHX compounds allows concatenating both steps without having to isolate 3'cisHX and without this affecting the process.

DETAILED DESCRIPTION OF THE INVENTION

This invention has as an object to provide a process for obtaining compounds derived from tetrahydro-β-carboline, specifically tadalafil (7)

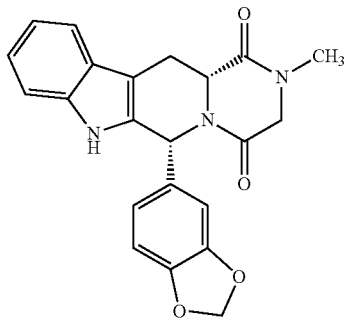

and intermediate products from the synthesis, comprising a process for producing compounds of formula 3'cisHX

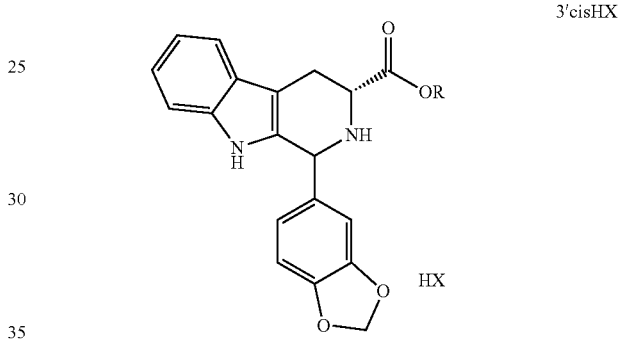

where R represents a methyl, ethyl, isopropyl, n-propyl, n-butyl or sec-butyl group and X represents chlorine or bromine, comprising the reaction of alkyl esters of D-tryptophan as salts with an HX hydracid with formula 1'HX

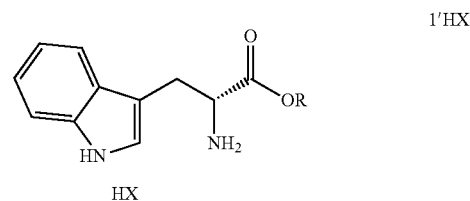

where R and X have the same meaning as in 3'cisHX and piperonal, of formula 2

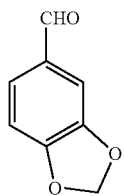

in the absence of any additional component and at a temperature comprised between 40 and 150° C. Preferably the molar ratio of 1'HX:2 is of 1:1 to 1:6, more preferably of 1:2 to 1:5.

In a preferred embodiment R is a methyl group and X is chlorine, with the preferred molar ratio of 1'HX:2 being 1:1 to 1:6, and more preferably 1:2 to 1:5.

In a preferred embodiment the reaction temperature is comprised between 75 and 150° C., more preferably between 110 and 130° C.

It is also an object of this invention to produce compounds derived from tetrahydro-β-carboline of formula 5'cis

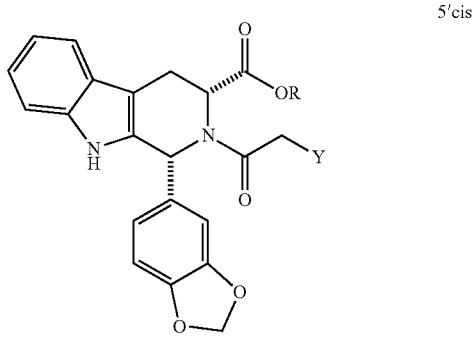

5'cis where R has the same meaning as in 1'HX and Y represents chlorine or bromine,
comprising the following steps:

(i) producing compounds of formula 3'cisHX, which may or may not be isolated from the reaction medium according to the process described above; and (ii) reaction of compounds of formula 3'cisHX with a haloacetyl halide (4')

4' where Y has the same meaning as in 5'cis and Z represents chlorine or bromine, in the presence of a basic agent and in an organic medium or in a mixture of an organic medium and water.

In a preferred embodiment Y and Z are both chlorine.

In another preferred embodiment, and without intending to limit the nature of the invention, the basic agent is a tertiary amine or an inorganic carbonate or an inorganic bicarbonate, regardless of the meanings stated above for Y and Z.

In another preferred embodiment, and without intending to limit the nature of the invention, the tertiary amine consists in butyldimethylamine, diethylmethylamine, diethylpropylamine, diisopropylethylamine, N-ethylmorpholine, N-ethylpiperidine, N-ethylpyrrolidin, N-methylmorpholine, N-methylpiperidine, N-methylpyrrolidin, tributylamine, triethylamine, triisopropylamine, trimethylamine and tripropylamine, the inorganic carbonate is sodium or potassium carbonate and the inorganic bicarbonate is sodium or potassium bicarbonate.

In another preferred embodiment, regardless of meanings stated above for Y and Z, and regardless of the tertiary amine or the inorganic carbonate or bicarbonate chosen, the organic medium is chosen, and without intending to limit the nature of the invention, from the group consisting of aliphatic alcohols such as ethanol, methanol, isopropanol, n-butanol, n-propanol or t-butanol, amides such as dimethylformamide, N-methylpyrrolidin or N,N-dimethylacetamide, ketones such as acetone, methylethylketone or methylisobutylketone, ethers such as diethyl ether, diethoxymethane, diisopropyl ether, 1,2-dimethoxyethane, dioxane, ethyl-t-butyl ether, methyl-t-butyl ether, tetrahydrofurane or tetrahydropyran, esters such as ethyl acetate, propyl acetate, isobutyl acetate, n-butyl acetate or ethyl formate, aliphatic halogenated hydrocarbons such as chloroform, 1,2-dichloroethane or dichloromethane, aromatic hydrocarbons such as toluene, 1,2-xylene, 1,3-xylene or 1,4-xylene, saturated hydrocarbons such as hexane, cyclohexane, heptane, methylcyclohexane or petroleum ether, nitriles such as acetonitrile or propionitrile and sulphoxides such as dimethyl sulphoxide, and mixtures thereof.

Preferably the organic medium is chosen from the group consisting of dichloromethane, tetrahydrofurane and ethyl acetate.

It is also the purpose of this invention to produce the compound derived from tetrahydro-β-carboline of formula 7 (tadalafil)

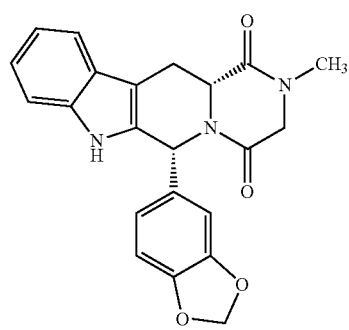

7 comprising the following steps:

(i) producing a compound of formula 5'cis according to the process described above; and (ii) reaction of the compound of formula 5'cis with methylamine (6) in an organic medium or in a mixture of an organic medium and water.

Preferably the organic medium is chosen, and without intending to limit the nature of the invention, from the group consisting of aliphatic alcohols such as ethanol, methanol, isopropanol, n-butanol, n-propanol or t-butanol, amides such as dimethylformamide, N-methylpyrrolidin or N,N-dimethylacetamide, ketones such as acetone, methylethylketone or methylisobutylketone, ethers such as diethyl ether, diethoxymethane, diisopropyl ether, 1,2-dimethoxyethane, dioxane, ethyl-t-butyl ether, methyl-t-butyl ether, tetrahydrofurane or tetrahydropyran, esters such as ethyl acetate, propyl acetate, isobutyl acetate, n-butyl acetated or ethyl formate, aliphatic halogenated hydrocarbons such as chloroform, 1,2-dichloroethane or dichloromethane, aromatic hydrocarbons such as toluene, 1,2-xylene, 1,3-xylene or 1,4-xylene, saturated hydrocarbons such as hexane, cyclohexane, heptane, methylcyclohexane or petroleum ether, nitriles such as acetonitrile or propionitrile and sulphoxides such as dimethyl sulphoxide, and mixtures thereof.

The invention is illustrated below with the following examples, which must not be understood as limiting of the scope of this invention.

EXAMPLES

Example 1

Production of methyl(1R,3R)-1-(3,4-methylenedioxyphenyl)-2,3,4,9-tetrahydro-9H-pyrido[3,4-b]-indol-3-carboxylate(3cisHCl)

50 g (0.3 mol) of piperonal (2) were heated to 110° C. 21.2 g (0.08 mol) of D-tryptophan methyl ester hydrochloride (1HCl) were added. The suspension was stirred for 15 minutes (min) at 110° C. A paste is formed that was allowed to cool to 70° C. and 210 ml of acetonitrile (ACN) were added. It was stirred for 1 h at 20-25° C. The solid was filtered, washed with 50 ml of ACN and dried under vacuum at 50° C. This produces 29.6 g of 3cisHCl (92% yield). HPLC Purity: 94% (3% trans isomer). Melting point 220° C. 1H NMR (400 MHz, DMSO) δ 10.83 (s, 1H), 10.78 (s, 1H), 10.34 (s, 1H), 7.53 (d, j=7.7 Hz, 1H), 7.30 (d, j=8.0 Hz, 1H), 7.18-6.98 (m, 5H), 6.10 (s, 2H), 5.88 (s, 1H), 4.70 (s, 1H), 3.83 (s, 3H), 3.34 (d, j=8.0 Hz, 2H). IR (KBr) vmax 3399, 3207, 3058, 3030, 2961, 2913, 2636, 2525, 2423, 2391, 1743, 1493, 1259, 1041, 746 cm$^{-1}$.

Example 2

Production of methyl(1R,3R)-1-(3,4-methylenedioxyphenyl)-2-chloroacetyl-2,3,4,9-tetrahydro-9H-pyrido[3,4-b]indol-3-carboxylate (5cis)

a) Starting from D-tryptophan methyl ester hydrochloride (1HCl)

100 g (0.67 mol) of piperonal (2) were heated to 120° C. 42.4 g (0.17 mol) of D-tryptophan methyl ester hydrochloride (1HCl) were added. The suspension was stirred for 30 min at 120° C. It was allowed to cool to 20-25° C. 380 ml of DCM were added. It was cooled to 0-5° C. and under a $N_2$ atmosphere, 56.8 ml of triethylamine (0.4 mol) were added dropwise (15 min). It was stirred at 0-5° C. for 15 min. 16 ml of chloroacetyl chloride (0.2 mol) were added dropwise (30 min) in 38 ml of DCM. It was stirred at 0-5° C. for 30 min. It was left to react at room temperature. 1272 ml of DCM were added. It is first extracted with deionised water (794 ml), and then with a saturated solution of $NaHCO_3$ (1272 ml) and finally with a saturated solution of NaCl (1590 ml). The organic phase was dried with $Na_2SO_4$, filtered, and the solvent evaporated under low pressure. It was recrystallised with a 4:1 mixture of IPA/water (380 ml) stirring for 2 h at room temperature. The precipitates obtained was filtered and washed with IPA and dried under vacuum at 50° C. This produced 55.87 g of 5cis (79% yield). HPLC Purity: 96.5%. Melting point 225° C. 1H NMR (400 MHz, DMSO) δ 10.88 (s, 1H), 7.55 (d, j=7.7 Hz, 1H), 7.29 (d, j=8.0 Hz, 1H), 7.11 (t, j=7.2 Hz, 1H), 7.03 (t, j=7.3 Hz, 1H), 6.91-6.72 (m, 2H), 6.65 (s, 1H), 6.47 (d, j=7.8 Hz, 1H), 5.98 (d, j=7.4 Hz, 2H), 5.21 (d, j=6.6 Hz, 1H), 4.85 (d, j=13.8 Hz, 1H), 4.45 (d, j=13.8 Hz, 1H), 3.48 (d, j=15.9 Hz, 1H), 3.16-2.95 (m, 4H). IR (KBr) vmax 3248, 3125, 3078, 2989, 2944, 2904, 1733, 1657, 1627, 1489, 1416, 1237, 1038, 747 cm$^{-1}$.

b) Starting from D-tryptophan methyl ester hydrochloride (1HCl)

59 g (0.39 mol) of piperonal (2) and 25 (0.098 mol) g of D-tryptophan methyl ester hydrochloride (1HCl) were added to a reactor. The mixture was heated to 85° C. and stirred at this temperature for 3 h. It was allowed to cool to 55-60° C. 160 ml of THF, 40 ml of water and 41 ml (mol) of TEA were added. It was stirred at 55-60° C. until complete dissolution. It was cooled to 0-10° C. and 14 ml of chloroacetyl chloride (0.17 mol) were added dropwise, dissolved in 15 ml of THF. It was stirred at 0-10° C. for 1 h. 150 ml of the mixture were distilled at a $T_{max}$ of 45° C. 240 ml of IPA and 60 ml of water were added. 50 ml of the mixture were distilled at a $T_{max}$ of 45° C. It was cooled to room temperature stirred for 2 h at said temperature. The precipitates obtained was filtered and washed with IPA and dried under vacuum at 50° C. This produced 36 g of 5cis (86% yield). HPLC Purity: 97.4%.

c) Starting from methyl(1R,3R)-1-(3,4-methylene-dioxyphenyl)-2,3,4,9-tetrahydro-9H-pyrido[3,4-b]-indol-3-carboxylate (3cisHCl)

50 g of 3cisHCl (0.13 mol) were suspended in a 4:1 mixture of 250 ml of THF/water. It was cooled to 0-5° C. 47 ml of triethylamine (0.34 mol) were added. Subsequently, 14.5 ml of chloroacetyl chloride (4) (0.18 mol) diluted in 30 ml of THF were added dropwise and without the temperature exceeding 10° C. It was stirred for 2 h at 0-10° C. and under a $N_2$ atmosphere. 70% of the solvent was evaporated under low pressure. 250 ml of a 4:1 mixture of IPA/water were added and 20% of the solvent was removed under low pressure. It was stirred for 1 h at 20-25° C. The precipitates obtained was filtered and washed with IPA and dried under vacuum at 50° C. This produced 51.3 g of 5cis (93% yield). HPLC Purity: 98.7%.

Example 3

Production of (6R,12R)-2,3,6,7,12,12a-hexahydro-2-methyl-6-(3,4-methylenedioxyphenyl)-pyrazino[2', 1':6,1]pyrido[3,4-b]indol-1,4-dione (7)

0.5 g of carboline chloroacetyl 5cis were dissolved in 2.5 ml of THF. 0.45 g of a 40% methylamine solution in water were added dropwise at 25° C. and under a $N_2$ atmosphere. It was heated to 55° C. stirred for 1 h. It was cooled to 0-5° C. and 3 ml of a 2:1 IPA/water mixture were added. Concentrated HCl was added until reaching an acid pH. The THF was distilled, cooled to 0-5° C. and 1.5 ml of IPA and 0.5 ml of water were added. It was stirred at 0-5° C. for 2 h. It was filtered and the solid obtained washed with a cold 1:1 mixture of IPA/water and dried under vacuum at 50° C. This produced 0.35 g of 7 (77% yield). HPLC Purity: 99.6%. Melting point 293° C. 1H NMR (400 MHz, DMSO) δ 11.03 (s, 1H), 7.55 (d, j=7.7 Hz, 1H), 7.31 (d, j=7.9 Hz, 1H), 7.06 (t, j=7.3 Hz, 1H), 7.00 (t, j=7.3 Hz, 1H), 6.88 (s, 1H), 6.83-6.73 (m, 2H), 6.15 (s, 1H), 5.92 (s, 2H), 4.40 (dd, j=11.5, 3.8 Hz, 1H), 4.18 (d, j=17.1 Hz, 1H), 3.94 (d, j=17.2 Hz, 1H), 3.53 (dd, j=15.8, 4.3 Hz, 1H), 3.04-2.95 (m, 1H), 2.93 (s, 3H). IR (KBr) vmax 3328, 3061, 2905, 2776, 1678, 1627, 1438, 1323, 1243, 1041, 749 cm$^{-1}$.

The invention claimed is:
1. A process for obtaining a tetrahydro-β-carboline compound of formula 3'cisHX

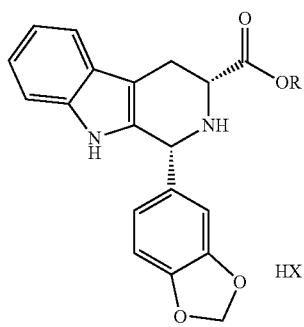

3'cisHX

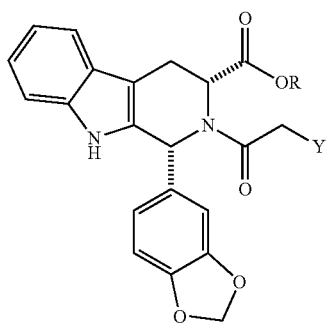

5'cis wherein R represents a methyl, ethyl, isopropyl, n-propyl, n-butyl or sec-butyl group and X represents chlorine or bromine, comprising reacting a D-tryptophan alkyl ester as a salt with an HX hydracid of formula 1'HX

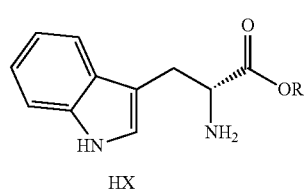

1'HX wherein R and X have the same meaning as in 3'cisHX and piperonal, of formula 2

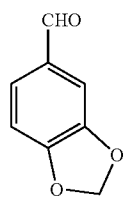

2 in the absence of any additional component and at a temperature between 40 and 150° C. to thereby obtain formula 3'cisHX.

2. The process according to claim 1, wherein R is a methyl group and X is chlorine.

3. The process according to claim 1, wherein a molar ratio of 1'HX:2 is from 1:1 to 1:6.

4. The process according to claim 3, wherein a molar ratio of 1'HX:2 is from 1:2 to 1:5.

5. The process according to claim 1, wherein the reaction temperature is between 75 and 150° C.

6. The process according to claim 5, wherein the reaction temperature is between 110 and 130° C.

7. A process for obtaining a tetrahydro-β-carboline compound of formula 5'cis wherein R has the same meaning as in 1'HX and Y represents chlorine or bromine, comprising the following steps:
(i) producing a compound of formula 3'cisHX, which optionally is isolated from the reaction medium according to the process described in claim 1; and
(ii) reacting a compound of formula 3'cisHX with a haloacetyl halide (4')

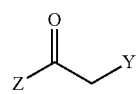

4' wherein Y has the same meaning as in 5'cis and Z represents chlorine or bromine, in the presence of a basic agent and in an organic medium or in a mixture of an organic medium and water to thereby obtain formula 5'cis.

8. The process according to claim 7, wherein Y and Z are both chlorine.

9. The process according to claim 7, where the basic agent is selected from at least one of the group consisting of a tertiary amine, an inorganic carbonate and an inorganic bicarbonate.

10. The process according to claim 9, wherein the tertiary amine is selected from at least one of the group consisting of butyldimethylamine, diethylmethylamine, diethylpropylamine, diisopropylethylamine, N-ethylmorpholine, N-ethylpiperidine, N-ethylpyrrolidin, N-methylmorpholine, N-methylpiperidine, N-methylpyrrolidin, tributylamine, triethylamine, triisopropylamine, trimethylamine and tripropylamine, wherein the inorganic carbonate is selected from at least one of the group consisting of sodium and potassium carbonate and wherein the inorganic bicarbonate is selected from at least one of the group consisting of sodium and potassium bicarbonate.

11. The process according to claim 7, wherein the organic medium is selected from at least one of the group consisting of an aliphatic alcohol, an amide, a ketone, an ether, an ester, an aliphatic halogenated hydrocarbon, an aromatic hydrocarbon, a saturated hydrocarbon, a nitrile, and a sulphoxide.

12. The process according to claim 11, wherein the organic medium is selected from at least one of the group consisting of an aliphatic halogenated hydrocarbon, an ether and an ester, wherein the aliphatic halogenated hydrocarbon is dichloromethane, the ether is tetrahydrofurane and the ester is ethyl acetate.

13. A process for producing a tetrahydro-β-carboline compound of formula 7 (tadalafil)

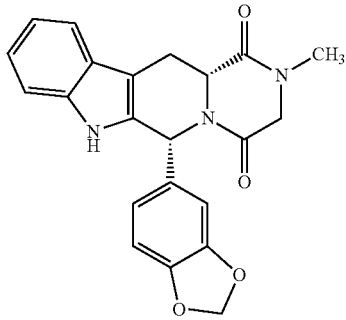

comprising the following steps:
(i) producing a compound of formula 5'cis according to the process described in claim 7; and
(ii) reacting the compound of formula 5'cis with methylamine (6) in an organic medium or in a mixture of an organic medium and water to thereby obtain a compound of formula 7.

14. The process according to claim 13, wherein the organic medium is selected from at least one of the group consisting of an aliphatic alcohol, an amide, a ketone, an ether, an ester, an aliphatic, halogenated hydrocarbon, an aromatic hydrocarbon, a saturated hydrocarbon, a nitrile and a sulphoxide.

15. The process according to claim 11,
wherein the aliphatic alcohol is selected from at least one of the group consisting of ethanol, methanol, isopropanol, n-butanol, n-propanol and t-butanol,
wherein the amide is selected from at least one of the group consisting of dimethylformamide, N-methylpyrrolidin and N,N-dimethylacetamide,
wherein the ketone is selected from at least one of the group consisting of acetone, methylethylketone and methylisobutylketone,
wherein the ether is selected from at least one of the group consisting of diethyl ether, diethoxymethane, diisopropyl ether, 1,2-dimethoxyethane, dioxane, ethyl-t-butyl ether, methyl-t-butyl ether, tetrahydrofurane and tetrahydropyran,
wherein the ester is selected from at least one of the group consisting of ethyl acetate, propyl acetate, isobutyl acetate, n-butyl acetated and ethyl formate,
wherein the aliphatic halogenated hydrocarbon is selected from at least one of the group consisting of chloroform, 1,2-dichloroethane and a dichloromethane,
wherein the aromatic hydrocarbon is selected from the group consisting of at least one of toluene, 1,2-xylene, 1,3-xylene and 1,4-xylene,
wherein the saturated hydrocarbon is selected from at least one of the group consisting of hexane, cyclohexane, heptane, methylcyclohexane and petroleum ether,
wherein the nitrile is selected from at least one of the group consisting of acetonitrile and propionitrile,
and wherein the sulphoxide is dimethyl sulphoxide.

16. The process according to claim 14,
wherein the aliphatic alcohol is selected from at least one of the group consisting of ethanol, methanol, isopropanol, n-butanol, n-propanol and t-butanol,
wherein the amide is selected from at least one of the group consisting of dimethylformamide, N-methylpyrrolidin and N,N-dimethylacetamide,
wherein the ketone is selected from at least one of the group consisting of acetone, methylethylketone and methylisobutylketone,
wherein the ether is selected from at least one of the group consisting of diethyl ether, diethoxymethane, diisopropyl ether, 1,2-dimethoxyethane, dioxane, ethyl-t-butyl ether, methyl-t-butyl ether, tetrahydrofurane and tetrahydropyran,
wherein the ester is selected from at least one of the group consisting of ethyl acetate, propyl acetate, isobutyl acetate, n-butyl acetated and ethyl formate,
wherein the aliphatic halogenated hydrocarbon is selected from at least one of the group consisting of chloroform, 1,2-dichloroethane and a dichloromethane,
wherein the aromatic hydrocarbon is selected from the group consisting of at least one of toluene, 1,2-xylene, 1,3-xylene and 1,4-xylene,
wherein the saturated hydrocarbon is selected from at least one of the group consisting of hexane, cyclohexane, heptane, methylcyclohexane and petroleum ether,
wherein the nitrile is selected from at least one of the group consisting of acetonitrile and propionitrile,
and wherein the sulphoxide is dimethyl sulphoxide.

* * * * *